(12) United States Patent
Horn et al.

(10) Patent No.: US 11,958,091 B2
(45) Date of Patent: Apr. 16, 2024

(54) FLUID DELIVERY DEVICES, SYSTEMS, AND METHODS

(71) Applicant: Ecolab USA Inc., Saint Paul, MN (US)

(72) Inventors: Katharina Horn, Ruhpolding (DE); Heribert Lohwieser, Siegsdorf (DE); Brock Mueggenborg, Saint Paul, MN (US)

(73) Assignee: Ecolab USA Inc., St. Paul, MN (US)

(*) Notice: Subject to any disclaimer, the term of this patent is extended or adjusted under 35 U.S.C. 154(b) by 834 days.

(21) Appl. No.: 17/046,748

(22) PCT Filed: Apr. 17, 2019

(86) PCT No.: PCT/US2019/027839
§ 371 (c)(1),
(2) Date: Oct. 9, 2020

(87) PCT Pub. No.: WO2019/204416
PCT Pub. Date: Oct. 24, 2019

(65) Prior Publication Data
US 2021/0162472 A1  Jun. 3, 2021

Related U.S. Application Data

(60) Provisional application No. 62/659,898, filed on Apr. 19, 2018.

(51) Int. Cl.
B08B 9/032 (2006.01)
A61M 39/22 (2006.01)
(Continued)

(52) U.S. Cl.
CPC ......... *B08B 9/0321* (2013.01); *A61M 39/225* (2013.01); *D06F 39/022* (2013.01);
(Continued)

(58) Field of Classification Search
CPC ..... G05D 7/0647; D06F 39/022; D06F 39/02; D06F 39/028; Y10T 137/0419;
(Continued)

(56) References Cited

U.S. PATENT DOCUMENTS 3,228,040 A  1/1966 Currie
4,428,208 A  1/1984 Krause
(Continued)

FOREIGN PATENT DOCUMENTS

DE  202005004855 U1  5/2005
DE  102007037883 A1  2/2009
(Continued)

OTHER PUBLICATIONS

International Patent Application No. PCT/US2019/027839, International Search Report and Written Opinion dated Sep. 6, 2019, 16 pages.
(Continued)

Primary Examiner — Jessica Cahill
(74) Attorney, Agent, or Firm — Fredrikson & Byron, P.A.

(57) ABSTRACT

Fluid delivery devices (114), systems (100), and methods are disclosed. A fluid delivery device (114) includes a body (115), a solution flow path (144), and a flush flow path (166). The solution flow path and the flush flow path are defined at the body. The solution flow path extends from a solution inlet (116), defined at the body, to a solution outlet (146), also defined at the body. The solution flow path includes a cross channel (148), an inlet channel (150), and an outlet channel (152). The inlet channel extends from the solution inlet to the cross channel. The outlet channel extends from the cross channel to the solution outlet. The flush flow path extends from a flush inlet (118), defined at the body, to a flush outlet (120), also defined at the body. The solution (Continued)

outlet fluidly connects the solution flow path to the flush flow path.

19 Claims, 6 Drawing Sheets

(51) Int. Cl.
 *B67D 1/07* (2006.01)
 *D06F 39/02* (2006.01)
 *A47L 15/44* (2006.01)
 *D06F 33/37* (2020.01)
(52) U.S. Cl.
 CPC .............. *A47L 15/44* (2013.01); *B67D 1/07* (2013.01); *D06F 33/37* (2020.02)
(58) Field of Classification Search
 CPC .......... Y10T 137/0424; Y10T 137/043; A47L 15/44; B08B 9/0321
 See application file for complete search history.

(56) References Cited

U.S. PATENT DOCUMENTS

| | | | |
|---|---|---|---|
| 5,379,749 A | 1/1995 | Rieke et al. | |
| 5,901,745 A | 5/1999 | Buchtel | |
| 7,413,433 B2 | 8/2008 | Blundy | |
| 7,501,283 B2 | 3/2009 | Hersch et al. | |
| 8,555,679 B2 * | 10/2013 | Schulze ................ | D06F 39/022 68/17 R |
| 9,801,505 B2 | 10/2017 | Buckalter et al. | |
| 11,634,851 B2 * | 4/2023 | Chae ..................... | D06F 39/028 68/17 R |
| 2005/0241675 A1 | 11/2005 | Jung et al. | |
| 2011/0290336 A1 | 12/2011 | Campbell et al. | |
| 2012/0024080 A1 * | 2/2012 | Carbone, II ............ | G01F 25/10 73/861.04 |
| 2016/0067660 A1 | 3/2016 | Tumini et al. | |
| 2017/0167068 A1 * | 6/2017 | Bao ...................... | B01F 25/3121 |
| 2019/0169778 A1 * | 6/2019 | Uchiyama ................ | D06F 39/08 |
| 2020/0346257 A1 * | 11/2020 | Saier ..................... | A47L 15/449 |

FOREIGN PATENT DOCUMENTS

| | | | | |
|---|---|---|---|---|
| EP | 2157341 A1 | 2/2010 | | |
| EP | 2832914 B1 | 12/2016 | | |
| WO | WO-2013156087 A1 * | 10/2013 | .............. | F04B 15/04 |
| WO | WO-2014187119 A1 * | 11/2014 | ........... | D06F 39/022 |

OTHER PUBLICATIONS

Peristaltic Pump for Auto Top-Off, Avast Marine Works, Retrieved online from <https://www.avastmarine.com/products/peristaltic-pump-for-auto-top-off> on Dec. 14, 2017, 7 pages.

* cited by examiner

FLUID DELIVERY DEVICES, SYSTEMS, AND METHODS

RELATED MATTERS

This application is a 35 U.S.C. 371 national phase filing from International Application No. PCT/US2019/027839, filed Apr. 17, 2019, which claims priority to U.S. Patent Application No. 62/659,898, filed Apr. 19, 2018. The entire contents of these applications are incorporated herein by reference.

TECHNICAL FIELD

This disclosure generally relates to fluid delivery devices, systems, and methods. More specifically, this disclosure relates to the delivery of a solution from a dispenser to a use device.

BACKGROUND

A dispenser is used to output a solution for use in a particular application. A number of different types of facilities employ dispensers for everyday applications. Such facilities can be found, for example, in the food and beverage, health care, and sanitation industries. The particular application in which the solution output by the dispenser is used varies across industries and can include, for example, use as a cleaning or sanitizing agent in laundry or warewashing applications.

Often times a number of dispensers can be used to output different types of solutions. The number of dispensers can output their respective, different solutions at different times onto a common line leading to a use device where the different solutions are employed. To avoid mixing the different solutions, it can be useful to flush the common line with water, or another flushing fluid. Moreover, often times it may be most efficient for dispensers to output solutions at a higher concentration than that designed for ultimate use at the use device and, accordingly, in some cases, it may also be useful to flush the common line to dilute such solutions.

A standalone flush manifold has been used to fluidly connect a number of dispensers to a fluid flush source. For each dispenser, a distinct hose is connected at one end to the dispenser and at another end to the flush manifold. The flush manifold extends along a length that includes a number of inlet connections for each of the distinct hoses as well as an inlet for the fluid flush source. However, this setup has a number of disadvantages. For one, the hose connecting each dispenser to the flush manifold is susceptible to wear and needs to be replaced frequently. This increases costs and is compounded by the existence of a distinct hose for each dispenser being used. Moreover, the hose, when connected to the flush manifold, tends to collect residual solution after a dispenser output, and, consequently, replacing the hose can create safety concerns relating to exposure to the residual solution. Furthermore, the flush manifold setup necessitates a large spatial footprint which is undesirable in many facilities where space is at a premium.

SUMMARY

In general, various exemplary embodiments relating to fluid delivery devices, systems, and methods are disclosed herein. As compared to previous fluid delivery products, various embodiments disclosed herein can be useful, for instance, in providing a more efficient fluid delivery capability. For example, embodiments disclosed herein can provide increased durability and, correspondingly, a longer useful life. At the same time, these embodiments can define a smaller footprint and thereby can have wider application, such as in facilities where space is limited. These embodiments can also reduce the amount of tubing and the number of sealing points as well as the collection of residual solution sump. This can lead to an increase in safety, for instance during servicing, while decreasing operational cost.

One exemplary embodiment includes a fluid delivery device. This embodiment of the fluid delivery device includes a body, a solution flow path, and a flush flow path. The solution flow path and the flush flow path are defined at the body. The solution flow path extends from a solution inlet, defined at the body, to a solution outlet, also defined at the body. The solution flow path includes a cross channel, an inlet channel, and an outlet channel. The inlet channel extends from the solution inlet to the cross channel. The outlet channel extends from the cross channel to the solution outlet. The flush flow path extends from a flush inlet, defined at the body, to a flush outlet, also defined at the body. The solution outlet fluidly connects the solution flow path to the flush flow path.

Another exemplary embodiment includes a method of delivering a solution. This embodiment of the method includes receiving the solution, conveying the solution, and delivering the solution. The solution is received at a solution inlet. The solution is conveyed along a solution flow path from the solution inlet to a solution outlet. The solution flow path, the solution inlet, and the solution outlet are defined at a body of a fluid delivery device. Conveying the solution along a solution flow path from the solution inlet to a solution outlet includes i) conveying the solution in a first direction from the solution inlet to a cross channel, ii) conveying the solution in a second direction along the cross channel, and iii) conveying the solution in a third direction from the cross channel to the solution outlet. The first direction is opposite the third direction and the second direction is different than the first and third directions. The solution is delivered from the solution outlet to a flush flow path. The flush flow path extends from a flush inlet to a flush outlet. The flush flow path, the flush inlet, and the flush outlet are defined at the body of the fluid delivery device. The solution is delivered from the solution outlet to the flush flow path within the body of the fluid delivery device.

An additional exemplary embodiment includes a fluid delivery system. This embodiment of the fluid delivery system includes a liquid solution dispenser, a fluid delivery device, and a solid solution dispenser. The liquid solution dispenser has an outlet and the liquid solution dispenser is configured to dispense a first solution at the outlet. The fluid delivery device has a body. The body defines i) a solution inlet fluidly connected to the outlet of the liquid solution dispenser, ii) a solution outlet, iii) a solution flow path extending from the solution inlet to the solution outlet, iv) a flush inlet fluidly connected to a fluid line, v) a flush outlet fluidly connected to the fluid line, and vi) a flush flow path extending from the flush inlet to the flush outlet. The solution outlet fluidly connects the solution flow path to the flush flow path such that the fluid delivery device is configured to receive the first solution at the solution inlet and deliver the first solution to the flush flow path. The solid solution dispenser is configured to dispense a second solution on the fluid line. The fluid delivery device is configured to receive the second solution at the flush flow path.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Figure 1:
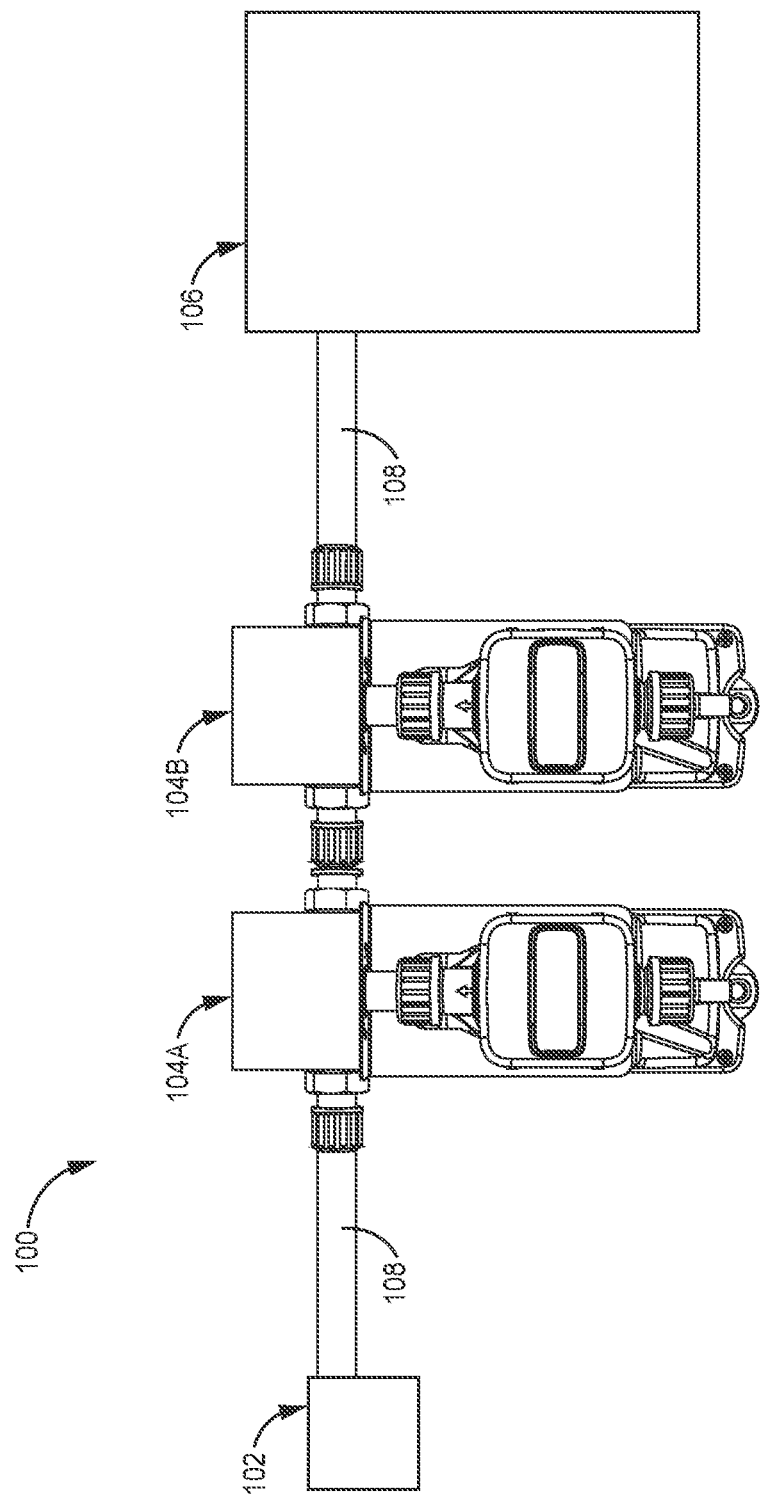
FIG. 1 is a schematic, illustrative diagram of an exemplary embodiment of a fluid delivery system.

FIG. 1 shows a schematic diagram of an exemplary embodiment of a fluid delivery system 100. The fluid delivery system 100 can include a fluid flush source 102, a first dispensing apparatus 104A, a second dispensing apparatus 104B, and a use device 106.

The fluid delivery system 100 can be used to convey one or more solutions from the first dispensing apparatus 104A and/or the second dispensing apparatus 104B to the use device 106 where the one or more solutions are employed. The first and second dispensing apparatuses 104A, 104B can be configured to dispense one or more solutions. For instance, the first dispensing apparatus 104A can be configured to dispense a first solution and the second dispensing apparatus 104B can be configured to dispense a second, different solution. The solution output by the first dispensing apparatus 104A and/or the second dispensing apparatus 104B can be conveyed to the use device 106 by a fluid line 108. The fluid flush source 102 can be configured to output a flushing fluid, such as water (e.g., without a chemistry that is in a solution output by the dispensing apparatus 104A and/or 104B) or another appropriate fluid, onto the fluid line 108. This flushing fluid can pass through the first and second dispensing apparatuses 104A, 104B and to the use device 106. The flushing fluid from the fluid flush source 102 can serve to flush the fluid line 108 of a solution (e.g., before a different solution is output onto the fluid line 108) and/or dilute a solution output onto the fluid line 108.

As shown in the illustrated embodiment, components of the fluid delivery system 100 are fluidly connected to convey one or more solutions to the use device 106 as described. Here, the first dispensing apparatus 104A is fluidly connected in-line, or in series, to the second dispensing apparatus 104B. In some such cases, the first dispensing apparatus 104A can be directly connected to the second dispensing apparatus 104B. In the illustrated case, a direct connection is made between a flush outlet of the first dispensing apparatus 104A and a flush inlet of the second dispensing apparatus 104B. In other cases (not illustrated here), the first dispensing apparatus 104A can be connected indirectly to the second dispensing apparatus 104B by the fluid line 108. In addition, the fluid flush source 102 is fluidly connected to the first dispensing apparatus 104A by the fluid line 108 and the second dispensing apparatus 104B is fluidly connected to the use device 106 by the fluid line 108. For instance, as shown here, the fluid line 108 can include a first fluid line connecting the fluid flush source 102 to the first dispensing apparatus 104A and a second fluid line connecting the second dispensing apparatus 104B to the use device 106. It is possible that, in some instances, the fluid flush source 102 can be directly connected to the first dispensing apparatus 104A and/or the second dispensing apparatus 104B can be directly connected to the use apparatus 106. In any case, in the illustrated system 100 flushing fluid from the fluid flush source 102 can pass through each of the first dispensing apparatus 104A and the second dispensing apparatus 104B.

As noted, one or more solutions from the first dispensing apparatus 104A and/or the second dispensing apparatus 104B are conveyed to the use device 106 where the one or more solutions are employed. The type of use device 106 can vary depending on the application in which the fluid delivery system 100 is utilized. For instance, as one example, the use device 106 can be a laundry machine or ware washing machine. Moreover, the type of one or more solutions output by the first and second dispensing apparatuses 104A, 104B can vary as suitable for the type of use device 106 present in a particular embodiment.

Figure 2:
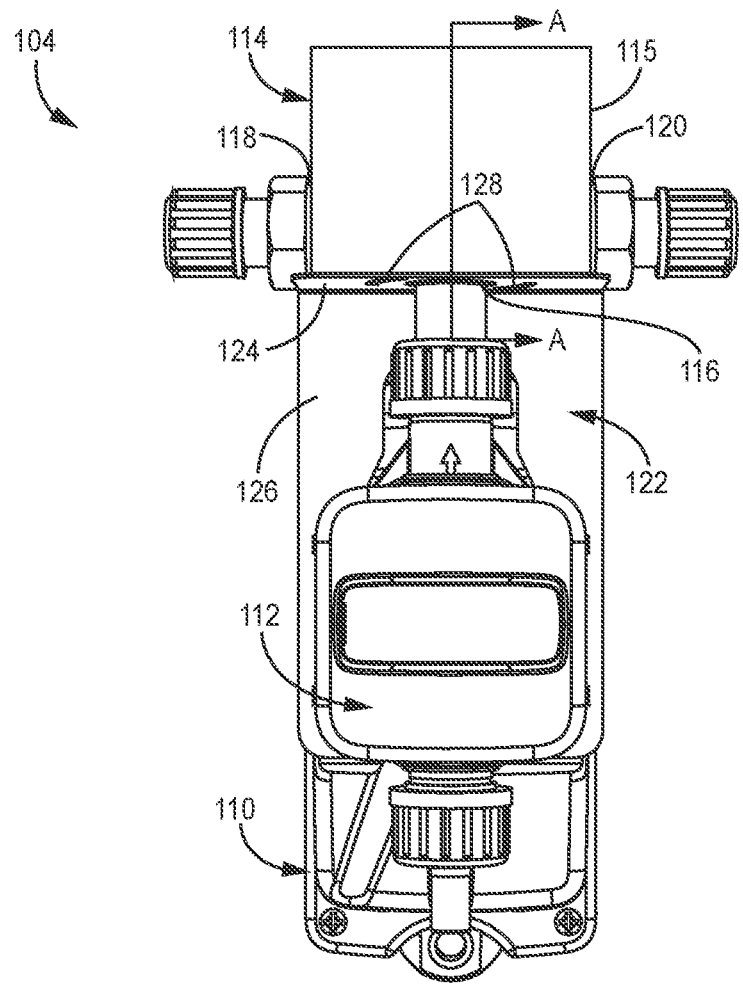
FIG. 2 is an elevational view of an exemplary embodiment of a dispensing apparatus that includes a dispenser, a pump, and a fluid delivery device. The exemplary embodiment of the dispensing apparatus can be used, for instance, as part of a fluid delivery system, such as that shown in FIG. 1.

FIG. 2 shows an elevational view of an exemplary embodiment of a dispensing apparatus 104. For example, the first dispensing apparatus and the second dispensing apparatus of the fluid delivery system described with reference to FIG. 1 can be the same as, or similar to, the dispensing apparatus 104 disclosed in reference to FIG. 2 herein.

The illustrated dispensing apparatus 104 includes a dispenser 110, a pump 112, and a fluid delivery device 114. The dispenser 110 can house a supply of the solution to be output from the dispensing apparatus 104 via the pump 112. For example, the dispenser 110 can be a liquid solution dispenser that holds a liquid chemistry thereat (e.g., in a container) which is used as the solution. As another example, the dispenser 110 can be a solid solution dispenser that houses a solid chemistry which is dissolved in water and used as the solution. In certain example, the dispenser 110 may also house motive and/or control components of the dispensing apparatus 104. For instance, the dispenser 110 can house a motor and electrical circuit board in addition to the solution. In other examples, the pump 112 can house such motive and/or control components. The pump 112 is coupled to the dispenser 110 and is configured to convey the solution from the dispenser 110 to the fluid delivery device 114 when signaled to do so (e.g., by the dispenser 110 or another, remote component). The pump 112 may receive motive power from the motor housed thereat, or in the dispenser 110, and pressurize the solution to an extent appropriate for conveying the solution to, and through, the fluid delivery device 114. The pump 112 can take a number of forms, such as a diaphragm pump or peristaltic pump as examples. The fluid delivery device 114 receives the solution from the pump 112 and outputs the solution from the dispensing apparatus 104.

The fluid delivery device 114 can include a body 115, a solution inlet 116, a flush inlet 118, and a flush outlet 120. As shown in the illustrated embodiment, the solution inlet 116, the flush inlet 118, and the flush outlet 120 are defined at a perimeter of the body 115 of the fluid delivery device 114. The solution inlet 116 can be configured to fluidly connect to the dispenser 110, via the pump 112, and receive thereat the solution to be output from the dispensing apparatus 104. The flush inlet 118 can be configured to fluidly connect to the fluid flush source (e.g., in some cases via another dispensing apparatus) and receive thereat the flushing fluid. The flush outlet 120 can be configured to fluidly connect to the use device (e.g., in some cases via another dispensing apparatus). The flush outlet 120 can be configured to output thereat the solution received at the solution inlet 116 as well as the flushing fluid received at the flush inlet 118. In this way, the fluid delivery device 114 can both pass the flushing fluid through, from the flush inlet 118 to the flush outlet 120, and output the solution, from the solution inlet 116 to the flush outlet 120.

In some cases, the fluid delivery device 114 can include a mounting bracket 122 that is adapted to secure the fluid delivery device 114 to the dispenser 110, such as via the pump 112 in the illustrated example. The mounting bracket 122 can include a plate 124 and an extension member 126. The plate 124 can interface with the body 115 of the fluid delivery device 114 and the extension member 126 can be configured to fixedly attach to the pump 112 and/or dispenser 110. The plate 124 can define a pair of curved slots 128 at which the body 115 of the fluid delivery device 114 is secured to the plate 124. The pair of curved slots can define an arc-shaped gap through the plate 124 where an attachment element, such as a screw, pin, or other appropriate fastener, can be received and secure the body 115 to the plate 124. The pair of curved slots 128 can define a length of the arc-shaped gap that provides space for the attachment element to securely move relative to the plate 124. As such, the pair of curved slots 128 can be adapted to allow the body 115 of the fluid delivery device 114 to pivot relative to the plate 124, and thus relative to the mounting bracket 122, pump 112, and/or dispenser 110. This may be useful is orienting the fluid delivery device 114 as needed for connection to an adjacent component in a fluid delivery system.

Figure 3:
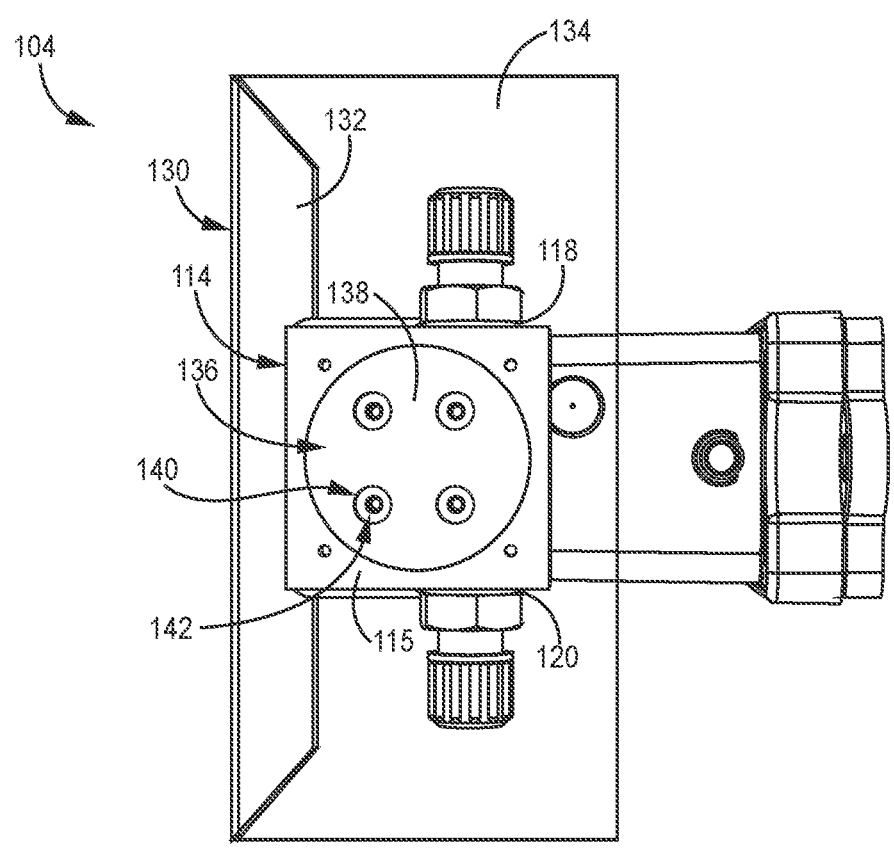
FIG. 3 is a top plan view of the exemplary embodiment of the dispensing apparatus of FIG. 2 further including a protective curtain.

FIG. 3 shows a top plan view of the exemplary embodiment of the dispensing apparatus 104 as shown and described in reference to FIG. 2. FIG. 3 further illustrates the presence of an exemplary protective curtain 130 associated with the dispensing apparatus 104. The protective curtain 130 can function as a safety measure, particularly where the solution(s) being conveyed by the fluid delivery device 114 are in relatively strong concentrations of chemistry that could be hazardous if inadvertently contacted with bare skin. The protective curtain 130 includes a first panel 132 and a second panel 134 connected to the first panel 132. As shown here, each of the first panel 132 and the second panel 134 can extend a width out from the fluid delivery device 114 a distance beyond the location of both the flush inlet 118 and the flush outlet 120. In addition, the first panel 132 can extend a length that is a distance beyond the location of the solution inlet. This can be help to reduce the risk of exposure to solution being conveyed at the dispensing apparatus 104 that may inadvertently emanate from the dispensing apparatus 104, such as during maintenance-related procedures.

FIG. 3 also illustrates a removable cover 136 of the fluid delivery device 114. The removable cover 136 has a first side 138 that forms an exterior surface of the body 115. The removable cover 136 also includes a fastening structure 140 for securing the removable cover 136 to the body 115. The fastening structure 140 of the removable cover 136 is configured to secure the removable cover 136 as such when the fastening structure 140 is aligned with a corresponding receiving structure 142 of the body 115. The fastening structure 140 and the receiving structure 142 can each be configured to allow the removable cover 136 to be secured to the body 115 only when one or more the corresponding features of the fastening structure 140 and the receiving structure 142 are aligned. This can help to ensure that a cross channel is appropriately configured when the removable cover 136 is being secured to the body 115. An example of a cross channel formed at least in part by a second side of the removable cover 136 is detailed further below in reference to that shown in FIG. 4. The presence of the removable cover 136 may be useful in facilitating periodic maintenance of the fluid delivery device 114 since it can allow relatively easy access to the interior of the fluid delivery device 114. In addition, in some cases, the removable cover 136 can facilitate improved manufacturing of the fluid delivery device 114.

Figure 4:
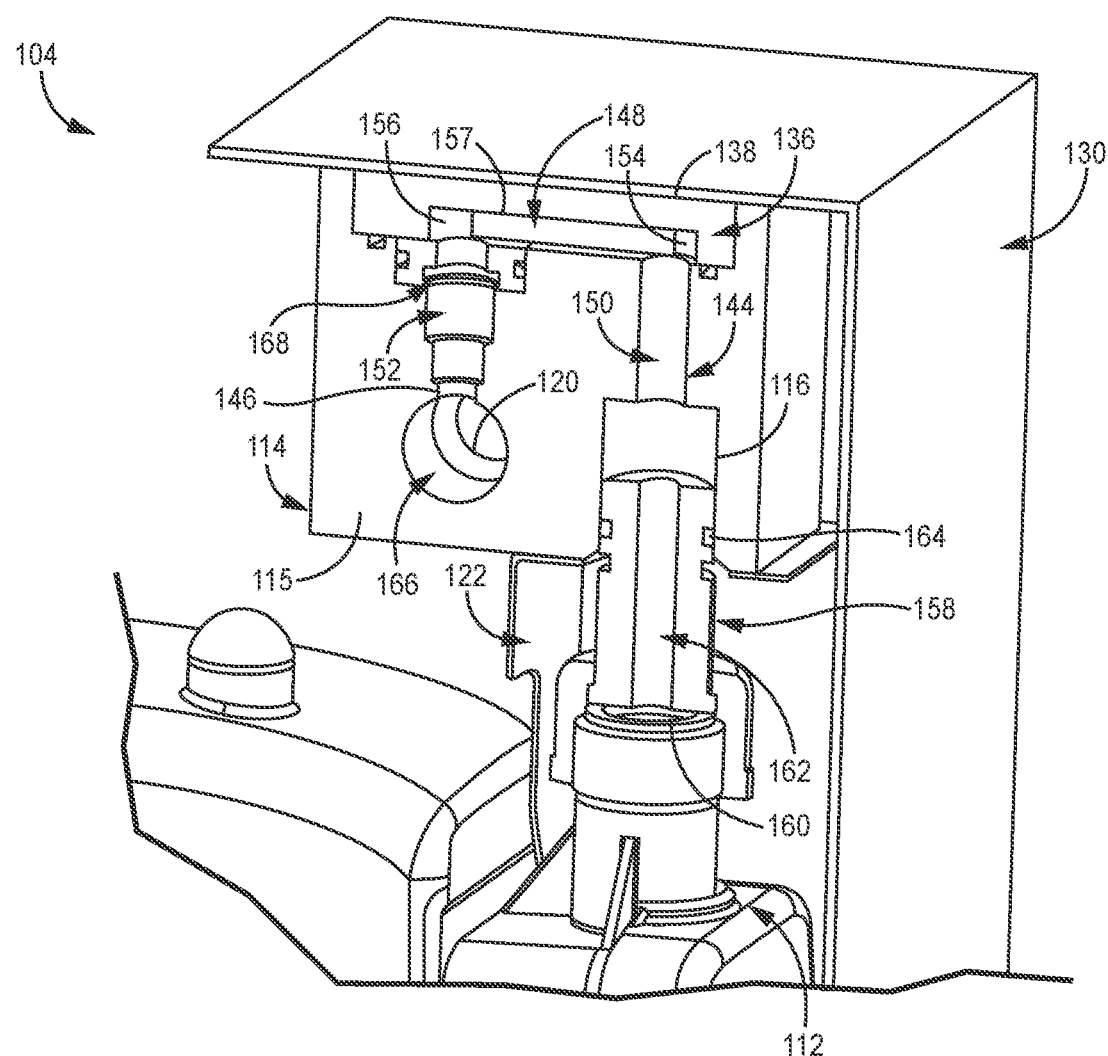
FIG. 4 is a cross-sectional view of the exemplary fluid delivery device taken along line A-A in FIG. 2.

FIG. 4 shows a cross-sectional view of the exemplary fluid delivery device 114. The cross-section shown in FIG. 4 is taken along line A-A in FIG. 2.

As shown in FIG. 4, the fluid delivery device 114 includes a solution flow path 144. In the illustrated embodiment, the solution flow path 144 is defined at the body 115. More particularly, in this embodiment, the solution flow path 144 is defined within the body 115. The solution flow path 144 extends from the solution inlet 116, defined at the body 115, to a solution outlet 146, defined at the body 115. More specifically, in this embodiment, the solution outlet 146 is defined within the body 115. The solution flow 144 path receives solution at the solution inlet 116 and conveys this solution to the solution outlet 146.

The solution flow path 144 includes a cross channel 148, an inlet channel 150, and an outlet channel 152. The inlet channel 150 extends from the solution inlet 116 to the cross channel 148. The outlet channel 152 extends from the cross channel 148 to the solution outlet 146. As shown in the illustrated embodiment, the orientation of the cross channel 148, the inlet channel 150, and the outlet channel 152 can generally form an inverted "U" shape (e.g., relative to the frame of reference shown in FIG. 4 where the fluid delivery device 114 can be viewed with the removable cover 136 as "top" and the solution inlet 116 as "bottom"). The cross channel 148 has a first cross channel end 154 and a second cross channel end 156. The cross channel 148 can extend along a cross channel axis running between the first cross channel end 154 and the second cross channel end 156. The inlet channel 150 can extend in a first direction from the first cross channel end 154 and the outlet channel 152 can extend in that first direction from the second cross channel end 156. In the present example, the inlet channel 150 extends along an inlet channel axis that is perpendicular to the cross channel axis. Also in the present example, the outlet channel 152 extends along an outlet channel axis that is perpendicular to the cross channel axis. The outlet channel 152 can extend along the outlet channel axis in the first direction while the cross channel 148 extends along the cross channel axis in a second direction that is different than the first direction.

In some examples, such as that shown here, the cross channel 148 of the solution flow path 144 can be formed, at least in part, by the removable cover 136. The removable cover 136 can have a second side 157 that is opposite the first side 138. The second side can form at least a portion of the cross channel 148. As noted, the fastening structure of the removable cover 136 is configured to secure the removable cover 136 to the body 115 when the fastening structure is aligned with a corresponding receiving structure of the body 115. This can also be useful in helping to ensure that the removable cover 136 is positioned relative to the body 115 so as to appropriately form the cross channel 148. Accordingly, the removable cover 136 and body 115 can be configured such that the second side 157 of the removable cover 136 forms at least the portion of the cross channel 148 when the fastening structure of the removable cover 136 is aligned with the receiving structure of the body 115.

The solution flow 144 path receives solution at the solution inlet 116 and conveys this solution along the inlet channel 150, the cross channel 148, and the outlet channel 152 to the solution outlet 146. To facilitate a fluid connection for receiving the solution, the solution inlet 116 can include a dispenser fitting 158. The dispenser fitting 158 can be adapted to fluidly connect the solution inlet 116 to an outlet of the dispenser, such as at an outlet 160 of the pump 112. The dispenser fitting 158 can define a dispenser fitting channel 162 having a dispenser fitting channel cross-sectional area that is constant along the length of the dispenser fitting channel 162. In some cases, this dispenser fitting channel cross-sectional area can be equal to a cross-sectional area of the inlet channel 150, which itself may be constant. Where the cross-sectional area of the inlet channel 150 and the cross-sectional area of the dispenser fitting channel 162 are equal, this can help to reduce, or eliminate, pressure drop of the solution when it is received at the fluid delivery device 114. The dispenser fitting 158 can include one or more sealing members 164, such as a gasket or O-ring, at an end thereof interfacing with the solution inlet 116 to help facilitate a fluid tight connection at the solution inlet 116.

In addition to the solution flow path 144, the fluid delivery device 114 also includes a flush flow path 166. In the illustrated embodiment, the flush flow path 166 is defined at the body 115. More particularly, in this embodiment, the flush flow path 166 is defined within the body 115. The flush flow path 166 extends from the flush inlet 118 (shown, e.g., in FIG. 2), defined at the body 115, to the flush outlet 120, defined at the body 115. As such, the flush flow path 166 can be configured to convey the flushing fluid through the fluid delivery device 114 from the flush inlet 118 to the flush outlet 120. Moreover, in the example shown, the solution outlet 146 fluidly connects the solution flow path 144 to the flush flow path 166. As noted previously, in the illustrated example the solution outlet 146 is defined within the body 115. As a result, the fluid connection between the solution flow path 144 and the flush flow path 166 is located within the body 115. In the illustrated embodiment, the axis of the outlet channel 152 is generally perpendicular to the flush flow path 166. Thus, in addition to the flush flow path 166 be configured to convey the flushing fluid, the flush flow path 166 can also be configured to convey the solution from the solution flow path 144 to the flush outlet 120.

One or more components can be included to selectively allow fluid communication between the flush flow path 166 and the solution flow path 144. In the embodiment shown here, a valve 168 is included at the fluid delivery device 114 to selectively allow fluid communication between the flush flow path 166 and the solution flow path 144. The valve 168 in this example is a check valve, such as a spring loaded ball valve. The check valve in this embodiment is disposed at the solution flow path 144. More particularly, the check valve is disposed within the outlet channel 152 such that the flush flow path 166 is located below, or downstream relative to solution flow direction along the solution flow path 144, the check valve. The check valve is configured to allow fluid communication from the solution flow path 144 to the flush flow path 166 but prevent fluid communication from the flush flow path 166 to the solution flow path 144. In this configuration, the valve 168 can be useful in helping to prevent flushing fluid from flowing through the solution flow path and to the pump 112 and/or dispenser 110.

The flush flow path 166 can define a flush flow path cross-sectional area. In the present embodiment, the flush flow path cross-sectional area is constant along its length from the flush inlet 118 (shown in, e.g., FIG. 2) to the flush outlet 120. Given that the flush flow path 166 may be configured to convey (e.g., sequentially or simultaneously) the solution, from the solution flow path 144, as well as the flushing fluid received at the flush inlet (which may be of a greater relative volume than the solution, depending on the application), the flush flow path cross-sectional area may be sized to accommodate this dual function. For instance, the flush flow path cross-sectional area may be greater than a cross-sectional area of some portions, or the entirety, of the solution flow path 144. As one particular example, the flush flow path cross-sectional area can be greater than the cross-sectional area of the inlet channel 150, which itself can in some cases be a generally constant cross-sectional area. As another particular example, the flush flow path cross-sectional area can be greater than the cross-sectional area of the outlet channel 152.

The features of the fluid delivery device 114 disclosed herein can provide a number of useful advantages. For example, the configuration of the solution flow path 144 and the flush flow path 166 can provide a number of these useful advantages as compared to prior fluid conveyance product configurations. For example, the fluid delivery device 114 can significantly reduce occurrence of residual solution collection, or sump, within the fluid delivery device 114. As another example, the amount of tubing needed to convey both solution and flushing fluid at the fluid delivery device, as well as in a fluid delivery system incorporating the fluid delivery device, can be significantly reduced. In addition, the number of sealing connections needing to be made, for instance during installation or maintenance, is reduced. These useful advantages can lead to an increase in safety while decreasing operational cost. Furthermore, the fluid delivery device 114 can provide a relatively confined means for outputting solution and conveying flushing fluid and thereby can allow its use in a larger number of applications where space is limited.

Figure 5:
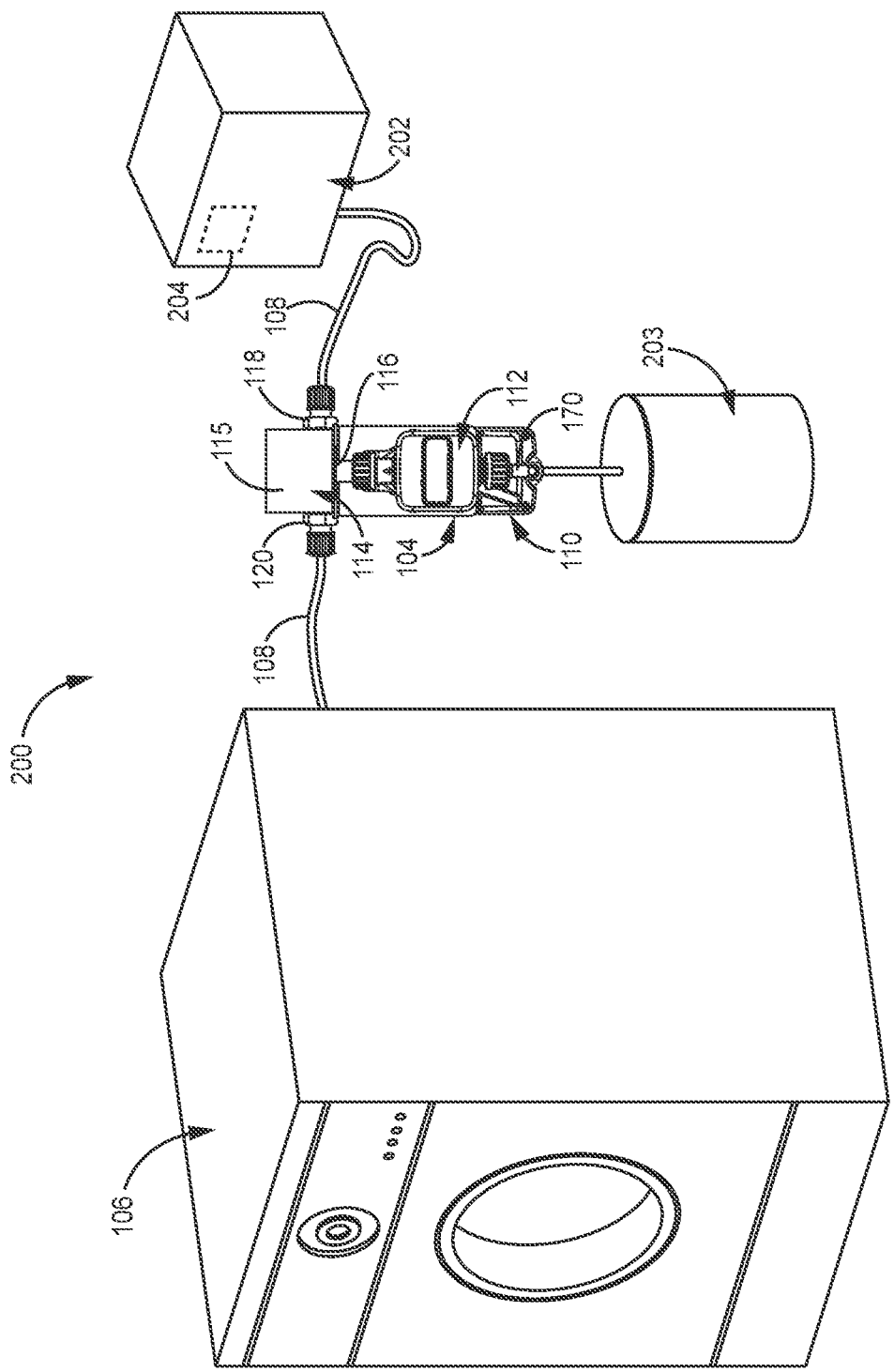
FIG. 5 is a schematic, exemplary illustration of another exemplary embodiment of a fluid delivery system.

FIG. 5 shows a schematic diagram of another exemplary embodiment of a fluid delivery system 200. The illustrated embodiment of the fluid delivery system 200 includes the dispensing apparatus 104, which has the dispenser 110, the pump 112, and the fluid delivery device 114, as disclosed elsewhere herein. The exemplary fluid delivery system 200 also includes a dispenser 202 and the use device 106. In some cases, as shown here, the fluid delivery system 200 can further include a solution supply 203. When included, the solution supply 203 can be fluidly connected to the dispensing apparatus 104 and supply solution (e.g., that includes a liquid chemistry) to the dispenser 110 for use in the fluid delivery system 200.

The fluid delivery system 200 can be used to convey one or more solutions from the dispensing apparatus 104 and/or the dispenser 202 to the use device 106 where the one or more solutions are employed. The dispensing apparatus 104 and the dispenser 202 can be configured to dispense one or more solutions. For instance, in the present embodiment, the dispensing apparatus 104 can be a liquid solution dispenser configured to dispense a first solution that includes a liquid chemistry and the dispenser 202 can be a solid solution dispenser configured to dispense a second solution that includes a solid chemistry dissolved in water. In some cases, the first solution dispensed by the dispensing apparatus 104 includes a different chemistry than the second solution dispensed by the dispenser 202.

As shown in the illustrated embodiment, components of the fluid delivery system 200 are fluidly connected to convey the one or more solutions to the use device 106. Each of the dispensing apparatus 104 and the dispenser 202 is fluidly connected to the use device 106, such as via the fluid line 108. As shown in this example, the dispensing apparatus 104 is fluidly connected in-line to the dispenser 202. As also shown in this example, the dispenser 202 disposed at the fluid line 108 at a first fluid line location that is upstream, relative to the flow direction in the fluid delivery system 200, from a second fluid line location of the dispensing apparatus 104. The fluid line 108, in the illustrated embodiment, fluidly connects the dispenser 202 to the dispensing apparatus 104 and fluidly connects the dispensing apparatus 104 to the use device 106. Though, in other examples, the dispenser 202 can be directly connected to the dispensing apparatus 104 and/or the dispensing apparatus 104 can be directly connected to the use device 106. In the illustrated embodiment, the dispenser 202 can be configured to dispense the second solution on the fluid line 108 to the use device 106 through the dispensing apparatus 104. Likewise, the dispenser 202 can be configured to output a flushing fluid, such as water or another appropriate fluid, on the fluid line 108 and through the dispensing apparatus 104. Thus, the second solution and/or the flushing fluid output from the dispenser 202 can pass through the dispensing apparatus 104 and to the use device 106. Also in the illustrated embodiment, the dispensing apparatus 104 can be configured to dispense the first solution on the fluid line 108 to the use device 106.

To facilitate conveyance of the one or more solutions and/or the flushing fluid, the dispensing apparatus 104 includes the fluid delivery device 114. The dispenser 110, of the dispensing apparatus 104, can include an outlet 170 at which the dispenser 110 is configured to dispense the first solution (e.g., that includes a liquid chemistry). The body 115 of the fluid delivery device 114 defines the solution inlet 116 that is fluidly connected to the outlet 170 of the dispenser 110, for instance via the pump 112. The fluid delivery device 114 is configured to receive the first solution at the solution inlet 116 and ultimately deliver the first solution to the fluid line 108. More particularly, as disclosed elsewhere herein, the body 115 of the fluid delivery device 114 defines a solution outlet (shown, e.g., in FIG. 4), a solution flow path extending (shown, e.g., in FIG. 4) from the solution inlet 116 to the solution outlet, a flush inlet 118 fluidly connected to the fluid line 108, a flush outlet 120 fluidly connected to the fluid line 108, and a flush flow path (shown, e.g., in FIG. 4) extending from the flush inlet 118 to the flush outlet 120. As also disclosed elsewhere herein, the solution outlet can fluid connect the solution flow path to the flush flow path.

Accordingly, the fluid delivery device 114 is configured to receive the first solution at the solution inlet 116 and convey the first solution along the solution flow path to the flush flow path and out the flush outlet 120 to the use device 106. In addition, the fluid delivery device 114 can be configured to receive the second solution and/or flushing fluid output by the dispenser 202. The fluid delivery device 114 can be configured to receive this second solution and/or flushing fluid at the flush inlet 118 and convey the second solution and/or flushing fluid along the flush flow path, defined at the body 115, to the use device 106. In this way, it is possible to place the dispensing apparatus 104 on an existing solid chemistry delivery line.

To operate fluid delivery system 200, the fluid delivery system 200 can include a controller 204. In the illustrated embodiment, the controller 204 is shown as part of the dispenser 202. Though, the controller 204 could instead be included as part of the dispensing apparatus 104 or as a stand-along component on the fluid delivery system 200. The controller 204 can include a user input mechanism (e.g., a keyboard, a touchscreen, etc.), a processor, computer-executable instructions run by the processor and stored in a non-transitory computer readable medium, and a communication mechanism (e.g., a receiver, a transceiver, etc.). The controller 204 can be in signal communication with dispensing apparatus 104 and the dispenser 202 as well as, in some further examples, the use device 106. In this way, the controller 204 can send one or more signals to the dispenser 202, the dispensing apparatus 104, and/or the use device 106. For instance, as one example, the controller can be in two-way signal communication with the dispenser 202, the dispensing apparatus 104, and/or the use device 106 such that the controller 204 can receive feedback from one or more of these components and send one or more signals to one or more of these components based on the feedback.

The controller 204 can send a signal to a component in the fluid delivery system 200 relating to a mode of operation of that particular component. As an example, the dispenser 202 can have multiple modes of operation as appropriate for a particular fluid delivery system. In one embodiment, the dispenser 202 has a first mode of operation during which the dispenser 202 is configured to dispense the second solution, on the fluid line 108, that includes a solid chemistry dissolved in water and a second mode of operation during which the dispenser 202 is configured to dispense a flushing fluid, such as water without the solid chemistry dissolved therein, on the fluid line 108. The controller 204 can be configured to send a signal to the dispenser 202 to operate in a select mode as appropriate for a fluid delivery sequence in the fluid delivery system 200.

As one example, the controller 204 can send signals related to modes of operation to both of the dispensing apparatus 104 and the dispenser 202. For instance, the controller 204 can be configured to send a first signal to the dispensing apparatus 104 to dispense the first solution (e.g., to the solution inlet 116 of the fluid delivery device 114). The controller 204 can also be configured to send a second signal to the dispenser 202 to dispense the second solution (e.g., to the fluid line 108). Furthermore, the controller 204 can be configured to send a third signal to the dispenser 202 to dispense the flushing fluid, such as water without the solid chemistry dissolved therein (e.g., on the fluid line 108). As noted, the controller 204 can, in some cases, send one or more of these signals based on feedback received from a component in the fluid delivery system, such as the use device 106. Moreover, the controller 204 can send these signals in a predetermined order to cause a fluid delivery sequence to be executed at the fluid delivery system 200. For instance, the controller 204 can be configured to send the third signal a predetermined amount of time after sending the first signal. Likewise, the controller 204 can be configured to send the second signal a predetermined amount of time before or after the sending the first signal.

Figure 6:
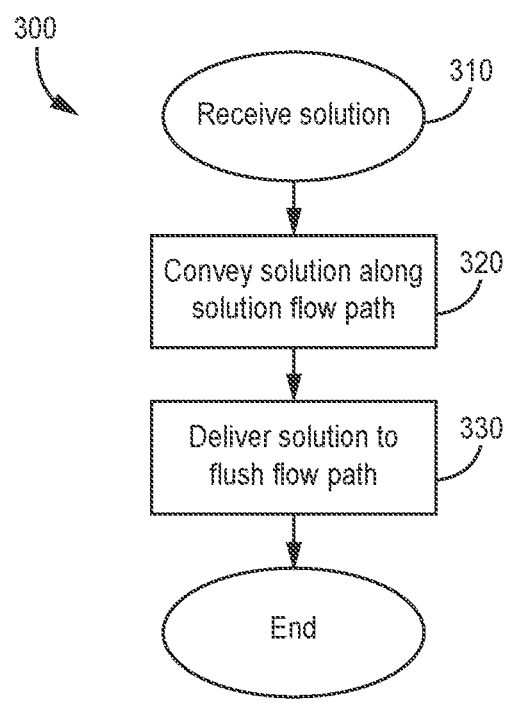
FIG. 6 is a flow diagram of an exemplary embodiment of a method of delivering a solution.

FIG. 6 shows a flow diagram of an exemplary embodiment of a method 300 of delivering a solution. At step 310, a solution is received. For example, the solution can be received at a solution inlet. This solution inlet can be a solution inlet of a fluid delivery device that is the same as, or similar to, the fluid delivery device disclosed herein. The solution received at step 310 can take a variety of forms, including a chemistry that is suited for application at a use device in a fluid delivery system. The chemistry included in the solution could be a liquid chemistry or a solid chemistry dissolved in water.

At step 320, the solution received at the solution inlet is conveyed along a solution flow path. The solution flow path can extend from a solution inlet to a solution outlet, for instance of a fluid delivery device that is the same as, or similar to, the fluid delivery device disclosed herein. The solution flow path, the solution inlet, and the solution outlet can be defined at a body of the fluid delivery device. Thus, at step 320, the solution can be conveyed along the solution flow path from the solution inlet to the solution outlet. In some cases, conveying the solution along the solution flow path at step 320 as such can include conveying the solution in a first direction from the solution inlet to a cross channel. This step may further include conveying the solution in a second direction along the cross channel and conveying the solution in a third direction from the cross channel to the solution outlet. In one example, the first direction can be opposite the third direction and the second direction can be different than both the first direction and third direction.

At step 330, the solution is delivered from the solution outlet to a flush flow path. The flush flow path can extend from a flush inlet to a flush outlet, for instance of a fluid delivery device that is the same as, or similar to, the fluid delivery device disclosed herein. The flush flow path, the flush inlet, and the flush outlet can be defined at the body of the fluid delivery device. Thus, at step 330, when the solution outlet is defined at the body of the fluid delivery device, the solution can be delivered from the solution outlet to the flush flow path within the body of the fluid delivery device. And, moreover, in this case, at step 330 the solution can be conveyed along the flush flow path and output at the flush outlet. This can allow the solution to then be utilized in an application, for instance being run at a use device in a fluid delivery system.

In a further embodiment of the method 300, a step can be included for conveying a flushing fluid along the flush flow path. The flushing fluid could be, for example, water without the chemistry entrained therein. The flushing fluid can be received at the flush inlet of the fluid delivery device. The flushing fluid can be conveyed through the fluid delivery device along the flush flow path, for instance after the solution is conveyed along the solution flow path at step 320 or after the solution is delivered to the flush flow path at step 330. In this way, the method 300 could include receiving a solution at one location on the fluid delivery device, receiving a flushing fluid at another, different location on the fluid delivery device, and delivering the solution and flushing fluid out from the fluid delivery device at a common location on the fluid delivery device.

Various non-limiting exemplary embodiments have been described. It will be appreciated that suitable alternatives are possible without departing from the scope of the examples described herein. These and other examples are within the scope of the following claims.

What is claimed is:

1. A fluid delivery device comprising:
a body;
a solution flow path defined at the body, the solution flow path extending from a solution inlet defined at the body to a solution outlet defined at the body, wherein the solution flow path comprises a cross channel, an inlet channel, and an outlet channel, the inlet channel extending from the solution inlet to the cross channel, the outlet channel extending from the cross channel to the solution outlet;
a removable cover having a first side forming an exterior surface of the body and a second side forming at least a portion of the cross channel, wherein the removable cover includes a fastening structure for securing the removable cover to the body when the fastening structure is aligned with a receiving structure of the body, and wherein the second side of the removable cover forms at least the portion of the cross channel when the fastening structure is aligned with the receiving structure; and
a flush flow path defined at the body, the flush flow path extending from a flush inlet defined at the body to a flush outlet defined at the body, wherein the solution outlet fluidly connects the solution flow path to the flush flow path.

2. The fluid delivery device of claim 1, wherein the cross channel has a first cross channel end from which the inlet channel extends in a first direction and a second cross channel end from which the outlet channel extends in the first direction.

3. The fluid delivery device of claim 2, wherein the cross channel extends along a cross channel axis in a second direction, wherein the outlet channel extends along an outlet channel axis in the first direction, the first direction being different than the second direction, and wherein the outlet channel axis is perpendicular to the flush flow path.

4. The fluid delivery device of claim 1, wherein the cross channel extends along a cross channel axis that is perpendicular to both an inlet channel axis along which the inlet channel extends and an outlet channel axis along which the outlet channel extends.

5. The fluid delivery device of claim 1, further comprising a check valve disposed within the solution flow path.

6. The fluid delivery device of claim 5, wherein the check valve is disposed within the outlet channel, and wherein the flush flow path is located below the check valve.

7. The fluid delivery device of claim 1, wherein the cross channel, the inlet channel, and the outlet channel form an inverted U shape.

8. The fluid delivery device of claim 1, wherein the solution flow path and the flush flow path are defined within the body.

9. The fluid delivery device of claim 8, wherein the solution outlet is defined within the body.

10. The fluid delivery device of claim 9, wherein the solution inlet, the flush inlet, and the flush outlet are defined at a perimeter of the body.

11. The fluid delivery device of claim 1, wherein the solution inlet comprises a dispenser fitting that is adapted to fluidly connect the solution inlet to an outlet of a dispenser.

12. The fluid delivery device of claim 11, wherein the dispenser fitting defines a dispenser fitting channel having a dispenser fitting channel cross-sectional area that is constant, wherein the inlet channel has an inlet channel cross-sectional area that is constant, and wherein the dispenser fitting channel cross-sectional area is equal to the inlet channel cross-sectional area.

13. The fluid delivery device of claim 11, further comprising a mounting bracket adapted to secure the fluid delivery device to the dispenser, wherein the mounting bracket includes a plate interfacing with the body of the fluid delivery device, and wherein the plate defines a pair of curved slots at which the body of the fluid delivery device is secured to the plate, the pair of curved slots adapted to allow the body of the fluid delivery device to pivot relative to the plate.

14. The fluid delivery device of claim 1, wherein the flush flow path has a flush flow path cross-sectional area that is constant, wherein the inlet channel has an inlet channel cross-sectional area that is constant, and wherein the flush flow path cross-sectional area is greater than the inlet channel cross-sectional area.

15. A method of delivering a solution, the method comprising the steps of:
receiving the solution at a solution inlet and conveying the solution along a solution flow path from the solution inlet to a solution outlet, the solution flow path, the solution inlet, and the solution outlet being defined at a body of a fluid delivery device, wherein conveying the solution along the solution flow path from the solution inlet to the solution outlet comprises i) conveying the solution in a first direction from the solution inlet to a cross channel, ii) conveying the solution in a second direction along the cross channel, and iii) conveying the solution in a third direction from the cross channel to the solution outlet, the first direction being opposite the third direction and the second direction being different than the first and third directions; and
delivering the solution from the solution outlet to a flush flow path, wherein the flush flow path extends from a flush inlet to a flush outlet, wherein the flush flow path, the flush inlet, and the flush outlet are defined at the body of the fluid delivery device, and wherein the solution is delivered from the solution outlet to the flush flow path within the body of the fluid delivery device.

16. A fluid delivery system comprising:
a liquid solution dispenser having an outlet, the liquid solution dispenser configured to dispense a first solution at the outlet;
a fluid delivery device having a body, the body defining i) a solution inlet fluidly connected to the outlet of the liquid solution dispenser, ii) a solution outlet, iii) a solution flow path extending from the solution inlet to the solution outlet, iv) a flush inlet fluidly connected to a fluid line, v) a flush outlet fluidly connected to the fluid line, and vi) a flush flow path extending from the flush inlet to the flush outlet, wherein the solution outlet fluidly connects the solution flow path to the flush flow path such that the fluid delivery device is configured to receive the first solution at the solution inlet and deliver the first solution to the flush flow path; and
a solid solution dispenser configured to dispense a second solution on the fluid line, wherein the fluid delivery device is configured to receive the second solution at the flush flow path.

17. The fluid delivery system of claim 16, wherein the solid solution dispenser has a first mode during which the solid solution dispenser is configured to dispense the second solution on the fluid line, the second solution comprising a solid chemistry dissolved in water, and a second mode during which the solid solution dispenser is configured to dispense water without the solid chemistry dissolved in water on the fluid line.

18. The fluid delivery system of claim 16, further comprising:
a controller in signal communication with the liquid solution dispenser and the solid solution dispenser, wherein the controller is configured to send a first signal to the liquid solution dispenser to dispense a first solution to the solution inlet of the fluid delivery device, and wherein the controller is configured to send a second signal to the solid solution dispenser to dispense a second solution to the fluid line.

19. The fluid delivery system of claim 18, wherein the solid solution dispenser is disposed at the fluid line at a first fluid line location that is upstream from a second fluid line location of the liquid solution dispenser, and wherein the controller is configured to send the second signal a predetermined amount of time after the controller sends the first signal.

* * * * *